United States Patent [19]
Aulie

[11] Patent Number: 5,376,135
[45] Date of Patent: Dec. 27, 1994

[54] ADJUSTABLE HYDRAULIC DAMPER

[76] Inventor: Alan L. Aulie, 3615 NW. Way, Redmond, Oreg. 97756

[21] Appl. No.: 22,526

[22] Filed: Feb. 25, 1993

[51] Int. Cl.⁵ .......................... A61F 2/64; A61F 2/74
[52] U.S. Cl. ................................ 623/43; 188/322.19; 188/314; 92/95
[58] Field of Search .................. 188/316, 322.19, 285; 623/26, 43-45; 92/95

[56] References Cited

U.S. PATENT DOCUMENTS

| | | | |
|---|---|---|---|
| 1,010,747 | 12/1911 | Gray | 188/285 |
| 1,160,976 | 11/1915 | Myers | 188/285 |
| 2,595,239 | 5/1952 | Gay | 188/316 X |
| 3,625,321 | 12/1971 | Lutz | 188/314 X |
| 4,502,366 | 3/1985 | Metz et al. | 89/43 R |
| 5,074,389 | 12/1991 | Slocum | 188/277 |
| 5,131,512 | 7/1992 | Steinhilber | 188/322.19 |

FOREIGN PATENT DOCUMENTS

| | | | |
|---|---|---|---|
| 0317981 | 1/1972 | U.S.S.R. | 188/285 |
| 1578388 | 7/1990 | U.S.S.R. | 188/322.19 |

Primary Examiner—David H. Willse
Attorney, Agent, or Firm—John F. Ingman

[57] ABSTRACT

An adjustable hydraulic damper involves a piston member operating within a hydraulic cylinder where the hydraulic cylinder wall is adjustably deformed to vary the annular space between a piston head and the inside cylinder wall through which hydraulic fluid must pass. The wall of the cylinder is adjustably deformed through an annular ramp formed circumferentially about the outside of the cylinder and having an angled bearing surface. A compression nut, having an angled inside circumferential surface, threadingly engages the outside of the cylinder, wherein rotation of the compression nut causes its angled inside surface to bear on the ramp of the cylinder wall, thereby producing a local, uniform, annular deformation of the inside surface of the cylinder wall. The amount of deformation, and thus the flow of fluid through the annular space, is adjustable by rotation of the compression nut. For bi-directional damping, with two opposing piston heads on the piston member, each piston head utilizes a separate compression nut. In such form, each piston head also includes an internal valve, formed of a plurality of longitudinal interior passageways valved by a flexible baffle, to permit free flow of fluid through the piston head not directly involved in the damping action. An accumulator, in the form of an annular foam ring, is positioned on the piston member in the low pressure region between the first piston head and the opposing second piston head to provide piston rod volume compensation.

10 Claims, 2 Drawing Sheets

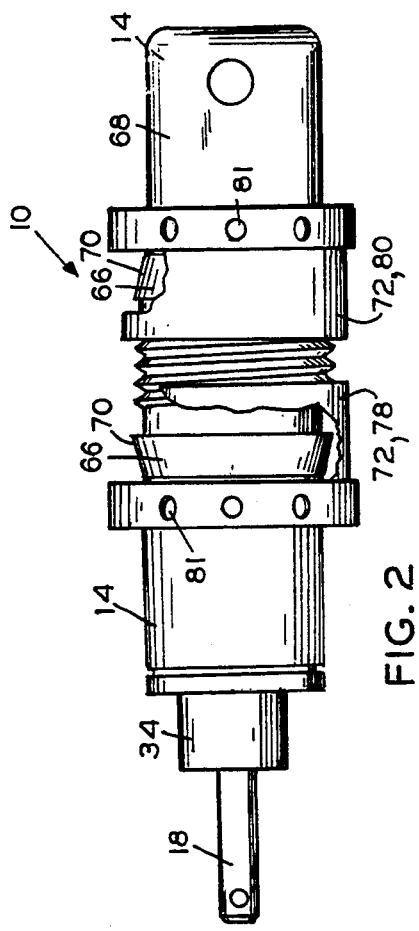
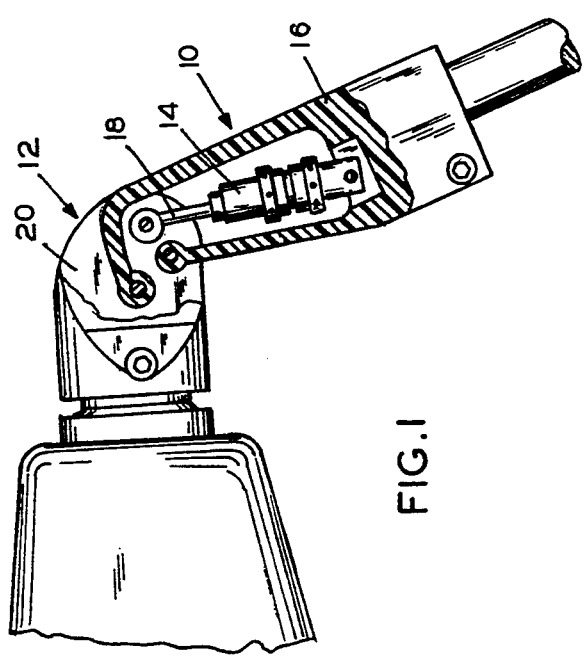
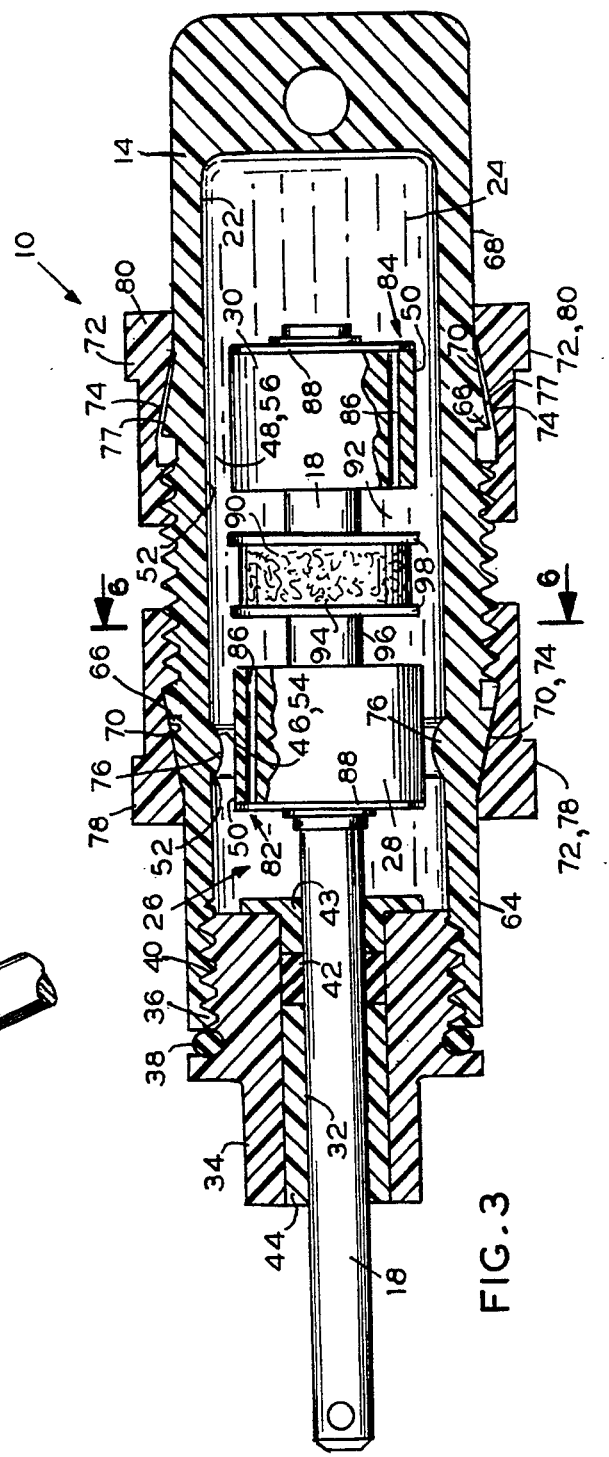

ADJUSTABLE HYDRAULIC DAMPER

BACKGROUND OF THE INVENTION

1. Field of the Invention

This invention involves an adjustable hydraulic damper. and, more particularly, a peripherally valved, bi-directional, hydraulic damper which is adjustable through external deformation of the hydraulic cylinder wall.

2. Description of the Prior Art

Previously developed adjustable hydraulic dampers have been complex in construction, utilizing external valves or ports, springs, positive sealing pistons, and other wearing parts. Such adjustable hydraulic dampers have experienced problems in reliability, cost, maintenance, and difficulty in adjustment. These shortcomings are particularly evident in the application of adjustable hydraulic dampers to prosthetic joints, particularly knee joints, where a compact, simple, reliable bi-directional damper, where the damping action is externally and separately adjustable in each direction, is needed.

SUMMARY OF THE INVENTION

The invention involves an adjustable hydraulic damper which is designed to meet the aforementioned need. The adjustable hydraulic damper involves a piston member operating within a hydraulic cylinder where the hydraulic cylinder wall is variably deformed to vary the annular space between a piston and the inside cylinder wall. An accumulator may be positioned between opposing dual pistons.

Accordingly, the adjustable hydraulic damper includes a cylinder with a longitudinal bore and a piston member which is moveable in the longitudinal bore within the cylinder. The piston member has at least one piston head wherein an annular space is defined by an outer cylindrical surface of the piston head and the inner wall of the cylinder, and serves as a peripheral valve through which hydraulic fluid within the cylinder passes upon movement of the piston member within the cylinder. The cylinder is formed of a deformable, resilient material wherein means for variably deforming the inner wall of the cylinder serve to vary the annular space of the peripheral valve, thereby controlling the flow of hydraulic fluid therethrough.

The deformable, resilient inner wall may be variably deformed through an annular ramp formed circumferentially about the outside wall of the cylinder and having an angled bearing surface. A portion of the outer wall is threaded so as to allow a compression nut, having an angled inside circumferential surface, to threadingly engage the outside wall of the cylinder, wherein rotation of the compression nut will cause its angled inside circumferential surface to bear on the annular ramp of the cylinder wall, thereby causing a local, uniform, annular deformation of the inside surface of the cylinder wall. The amount of deformation, and thus the annular space of the peripheral valve is controlled by rotation of the compression nut.

The preferred embodiment of the adjustable hydraulic damper utilizes two opposing piston heads on the piston member, each piston head utilizing a separate peripheral valve to control movement for a specific direction of movement, inward or outward, of the piston member. Thus, in the preferred embodiment, there are two separately adjustable compression nuts, each controlling a specific direction of movement. In addition to the peripheral valve about the piston head, each piston head includes an internal valve formed of a plurality of valved longitudinal interior passageways wherein the valving is provided by a flexible baffle located adjacent to, and operating upon, the longitudinal interior passageways. With movement of the piston member in a first direction, the internal valve of the first piston head is closed with hydraulic fluid flowing through the peripheral valve, and the internal valve of the second piston head is open with the hydraulic fluid flowing essentially unimpeded through the internal valve of the second piston head.

An accumulator, preferably in the form of an annular ring of compressible, closed cell neoprene foam, is positioned on the piston member between the first piston head and the opposing second piston head to provide piston rod volume compensation, that is, to compensate for varying volume available for hydraulic fluid within the hydraulic cylinder as the piston rod moves into and out of the cylinder.

BRIEF DESCRIPTION OF THE DRAWINGS

FIG. 1 illustrates the adjustable hydraulic damper in use within a prosthetic knee joint.

FIG. 2 illustrates an external side view of the adjustable hydraulic damper, with a portion cut away to show an annular ramp.

FIG. 3 illustrates a cross-sectional side view of the adjustable hydraulic damper, with the deformation of the cylinder wall greatly exaggerated for clarity.

DESCRIPTION OF THE PREFERRED EMBODIMENT

Figure 4:
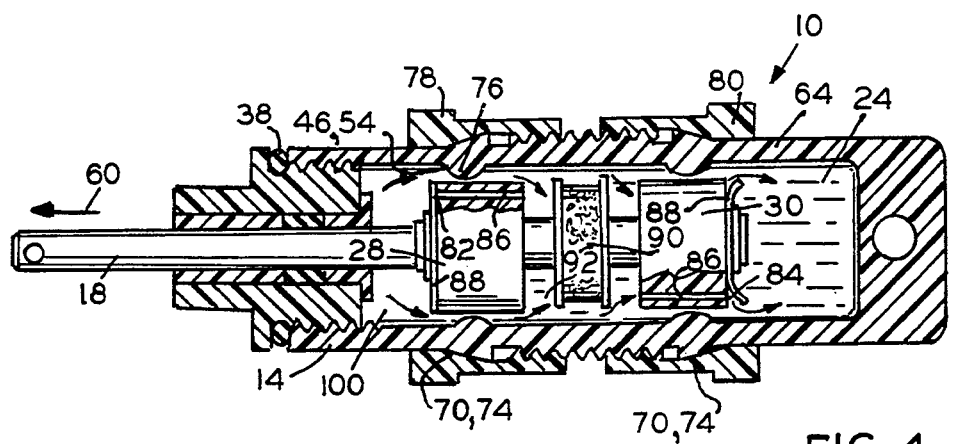
FIG. 4 illustrates a cross-sectional side view of the adjustable hydraulic damper, similar to FIG. 3, with the piston member moving outward from the hydraulic cylinder.

Turning now to the drawings, there is shown in FIG. 1 one possible use of the adjustable hydraulic damper 10 in a prosthetic knee joint 12, where a simple, bi-directional hydraulic damper, having separate, externally adjustable damping rates in either direction, finds beneficial use. As shown, the hydraulic cylinder 14 attaches to the lower or shank end 16 of the knee joint 12 while the piston rod 18, movably extending from the hydraulic cylinder 14, attaches to the upper or stump socket end 20 thereof. As the knee joint 12 is bent, the piston rod 18 moves outward from the hydraulic cylinder 14 while straightening of the knee joint 12 causes the piston rod 18 to insert into the hydraulic cylinder 14. As will be appreciated by those familiar with prosthetic joints and particularly prosthetic knee Joints 12, controlled damping of the movement of the knee Joint 12 is essential, with different damping rates and resistances used for extension and bending of the knee Joint 12.

Simple external adjustments, allowing variation by the user of the damping rates, is a highly beneficial characteristic, as is simplicity of the damping mechanism, reliability, and relatively low cost. Other uses of the present adjustable hydraulic damper design will become evident in areas where similar operational requirements exist. As illustrated, the adjustable hydraulic damper is used with the prosthetic hinge structure found in U.S. Pat. No. 5,171,325.

Figure 5:
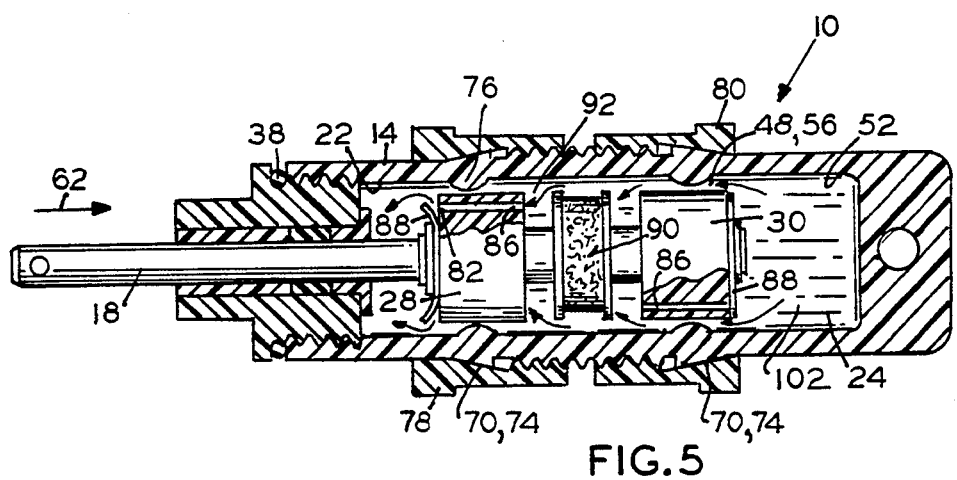
FIG. 5 illustrates a cross-sectional side view of the adjustable hydraulic damper, similar to FIG. 3, with the piston member moving inward into the hydraulic cylinder.
Figure 6:
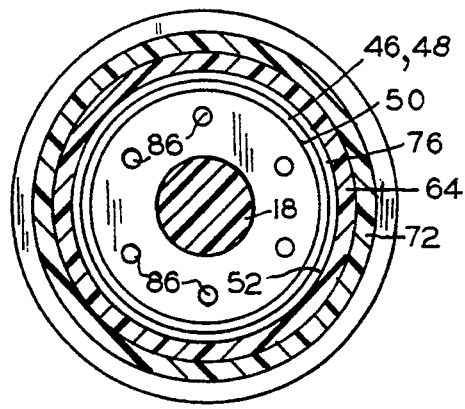
FIG. 6 illustrates illustrates a cross-sectional view of the adjustable hydraulic damper, as seen at line 6—6 of FIG. 3.
Figure 7:
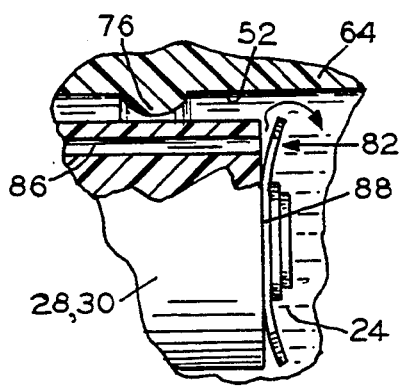
FIG. 7 illustrates a partial cross section of a piston head of the adjustable hydraulic damper, showing an internal valve allowing passage of the hydraulic fluid through longitudinal passageways within the piston head.

FIG. 2 illustrates an external view of a preferred embodiment of the adjustable hydraulic damper 10 while FIG. 3 provides a cross sectional view illustrating construction. FIGS. 4 and 5 provide additional cross-section views showing operation during movement of the piston rod 18. A hydraulic cylinder 14 having a longitudinal bore 22 formed therein contains an essentially noncompressible hydraulic fluid 24, such as a silicon fluid. The Dow Corning 200 silicone fluid, with a viscosity of 1000 centistokes, manufactured by Dow Corning Corporation, Midland, Mich. works well. A piston member 26 includes, in the preferred embodiment, two separated and opposing piston heads 28 and 30 which are affixed to a piston rod 18. The piston rod 18 slidingly extends through an opening 32 in a threaded plug 34 which closes the open end 36 of the hydraulic cylinder 14. An O-ring seal 38 is used to prevent leakage past the threads 40 while a conventional shaft seal 42, held in position by a seal retainer 43, is installed within the plug 34 to prevent leakage past the sliding piston rod 18. If the plug 34 is formed of a readily wearable material, it may be desirable to utilize a bushing 44 within the plug 34 to prevent wear at the opening 32.

The adjustable hydraulic damper 10 functions by controlling the annular leakage about the piston member 26 within the hydraulic cylinder 14. As indicated above, the preferred embodiment utilizes a piston member 26 which has two opposing piston heads 28, 30 which are fixed to the piston rod 18 in separated positions, as illustrated. An annular space 46, 48 is defined by an outer cylindrical surface 50 of each piston head 28, 30 and the inner surface 52 of the hydraulic cylinder 14, each annular space 46, 48 serving as a peripheral valve 54, 56 through which hydraulic fluid 24 within the hydraulic cylinder 14 passes upon movement of the piston member 26. Adjustment of the width of this annular space 46, 48 controls the flow of hydraulic fluid 24 past the piston head 28, 30, thus controlling the damping resistance provided. With two separate piston heads 28, 30, the peripheral valve 54 of one piston head 28 may be dedicated to controlling damping resistance on an outward stroke 60 of the piston member 26 and the peripheral valve 56 of the second piston head 30 used for controlling damping resistance on the inward stroke 62, there being distinct and separate control for each direction of movement of the piston rod 18 and thus the piston member 26.

In the drawings, the width of the annular space 46, 48, as well as the deformation 76 of the inner surface 52 of the cylinder wall, as discussed subsequently, is greatly exaggerated for illustrative purposes. In the preferred embodiment, as used with the prosthetic knee joint 12, a maximum width of the annular space 46, 48 of 0.006-inch has worked well.

In the present invention, the annular space 46, 48 of the peripheral valve 54, 56 of each piston head 28, 30 is varied by deforming, as desired, the inner surface 52 of the hydraulic cylinder 14 at the location of the piston head 28, 30. The hydraulic cylinder 14, or at least the cylinder wall 64, is formed of a deformable, resilient material, such as DELRIN, a structural thermoplastic manufactured by DuPont, Grenloch, N.Y. The preferred means of variably deforming the inner surface 52 of the cylinder wall 64 is the use of an annular ramp 66, formed circumferentially about the outer surface 68 of the hydraulic cylinder 14 and having an angled bearing surface 70. A bearing surface 70 of the preferred ramp 66 having an angle of 10 degrees relative to the outer surface 68 of the cylinder wall 64 works well in the prosthetic application of FIG. 1. A portion of the outer surface 68 of the cylindrical wall 64 is threaded so as to allow a nut member, in the form of a compression nut 72 having an angled inside circumferential surface 74, to threadingly engage the outer surface 68 of the hydraulic cylinder 14. Upon rotation of the compression nut 72, its angled inside circumferential surface 74 will bear upon the annular ramp 66 on the cylinder wall 64, thereby causing a local, uniform, annular inward-extending deformation 76 of the inner surface 52 of the cylinder wall 64. The amount of deformation 76, and thus the annular space 46, 48 of the peripheral valve 54, 56 is controlled by the adjustable position of the compression nut 72. The deformation 76 of the cylinder wall 64 is well below the elastic limits of the cylinder wall 64 material, so that, without pressure from the surface 74 of the compression nut 72, the cylinder wall 64 recovers to its original shape and thus original leakage and damping, whenever the compression nut 72 is loosened. In FIG. 3, annular space 46, corresponding to piston head 28 is shown reduced by the deformation 76 of the inner surface 52, while annular space 48 contrastingly remains in its original cylindrical shape, the compression nut 80 at the annular space 48 being loose, as evidenced by a gap 77 between surface 74 of compression nut 80 and surface 74 of the annular ramp 66.

The preferred embodiment of the adjustable hydraulic damper 10 utilizes two opposing piston heads 28, 30 on the piston member 26, each piston head 28, 30 utilizing a separate peripheral valve 54, 56 to control movement for a specific direction of movement, outward 60 or inward 62, of the piston member 26. Thus, in the preferred embodiment, there are two separately adjustable compression nuts, 78 and 80, each controlling a specific direction of movement. As illustrated, the compression nuts 78, 80 may be rotated by inserting a short rod (not shown) in a circumferential plurality of openings 81, the rod providing sufficient leverage to rotate the compression nuts 78, 80 about the hydraulic cylinder 14. In addition to the peripheral valve 54, 56 about the piston head 28, 30, each piston head 28, 30 includes an internal valve 82, 84 formed of a plurality of valved longitudinal interior passageways 86 wherein the valving is provided by a flexible, circular baffle 88 located adjacent to, and operating upon, the longitudinal interior passageways 86.

Thus, with movement of the piston member 26 in an outer direction 60, as seen in FIG. 4, the baffle 88 acts upon the interior passageways 86 so that the internal valve 82 of the piston head 28 is closed, with hydraulic fluid 24 flowing only through the peripheral valve 54, with annular space 46; and the internal valve 84 of the piston head 30 is open by the disengagement, as by bending, due to internal pressure, of its baffle 88, with the hydraulic fluid 24 flowing therethrough essentially unimpeded. As seen in FIG. 5, with the movement of the piston member 26 in an inner direction 62, the functions of the piston heads 28, 30 are reversed, with the peripheral valve 56, with annular space 48, controlling the damping resistance and the hydraulic fluid 24 flowing freely through the internal valve 82 of the piston head 28.

An accumulator 90 is used to compensate for changes of volume available for hydraulic fluid 24 within the hydraulic cylinder 14 as the piston member 26, and particularly the piston rod 18, moves longitudinally into and out of the hydraulic cylinder 14. The accumulator 90 may be formed of a compressible, closed cell neoprene foam, which contracts in volume to compensate for the additional volume of the piston rod 18 as the piston rod 18 moves into the hydraulic cylinder 14, and which expands as the piston rod 18 moves out of the hydraulic cylinder 14. In the present invention, the accumulator 90 is located in the low-pressure central region 92 between the piston heads 28, 30. In the preferred embodiment, the accumulator 90 is in the shape of an annular ring 94 which encircles the central portion 96 of the piston rod 18 extending between, and connecting, the spaced piston heads 28, 30. The annular ring 94 is held in place by a pair of transverse, annular flanges 98 attached to the central portion 96 of the piston rod 18. Since the accumulator 90 is never in the high-pressure region 100 in front of the piston head 28 during outward movement 60 of the piston member 26, nor in the high-pressure region 102 in front of the piston head 30 during inward movement 62 of the piston member 26, the elasticity of the accumulator 90 material does not influence the damping rate of the adjustable hydraulic damper 10, as it would if the accumulator 90 were located in the high-pressure regions 100, 102 of the piston heads 28 and 30 respectively.

The use of a central low-pressure region 92 has the significant additional advantage of attracting and retaining any air contamination within the hydraulic fluid 24, where the air, in the form of bubbles, would act in accumulator fashion themselves. The collection of air contamination in a low-pressure central region 92 reduces the serious degradation of damping characteristics associated with aerated hydraulic fluid 24 in the high pressure regions 100 and 102.

It is thought that the adjustable hydraulic damper of the present invention and its many attendant advantages will be understood from the foregoing description and that it will be apparent that various changes in form, construction and arrangement of the parts thereof may be made without departing from the spirit and scope of the invention or sacrificing all of its material advantages, the form hereinbefore described being merely an exemplary embodiment thereof. Clearly, the adjustable hydraulic damper would work in a variety of damper sizes with various diameters, strokes, volumes, speeds, fluids, and numbers of controlled regions for damping rates which vary with stroke position. Specifically, the adjustable hydraulic damper may have application in extremely small, even microscopic, applications.

I claim:

1. An adjustable hydraulic damper apparatus for use with a prosthetic knee Joint having a first section and a second section which are hingedly joined, the adjustable hydraulic damper apparatus comprising:
   a. a hydraulic cylinder, having a longitudinal bore forming a cylinder wall having an inner surface and an outer surface, said cylinder wall being formed of a resilient material; said hydraulic cylinder adapted to be attached to said first section of said prosthetic knee joint;
   b. hydraulic fluid located within said longitudinal bore of said hydraulic cylinder;
   c. a piston member, including:
      (1) two opposing piston heads, a first piston head and a second piston head; said piston heads being longitudinally movable in said longitudinal bore;
      (2) each piston head additionally having an internal valve formed of a plurality of longitudinal interior passageways and a flexible baffle located adjacent to an end of said longitudinal interior passageways; and
      (3) a piston rod which extends from said hydraulic cylinder and is adapted to be attached to said second section of said prosthetic knee joint;
   d. wherein an annular space is defined by an outer cylindrical surface of each said piston head and said inner surface of said cylinder wall, said annular space forming a peripheral valve through which said hydraulic fluid passes upon movement of said piston heads within said hydraulic cylinder; and
   e. means for variably deforming said inner surface of said cylinder wall, thereby varying said annular space of said peripheral valve, which include:
      (1) an annular ramp formed circumferentially about, and extending outward of, said outer surface of said cylinder wall, said annular ramp having an angled bearing surface;
      (2) a threaded portion on said outside surface of said cylinder wall;
      (3) a nut member, internally threaded to rotatingly engage said threaded portion on said outside surface of said cylinder wall, said nut member having an angled inside circumferential surface formed to bear, when said nut member is rotated, upon said angled bearing surface of said annular ramp;
      (4) said cylinder wall being formed, when said angled surface of said nut member bears upon said bearing surface of said annular ramp, to create an annular deformation of said inside surface of said cylinder wall;
      (5) said annular deformation having a magnitude controlled by the rotation of said nut member.

2. The adjustable hydraulic damper apparatus for use with a prosthetic knee joint, as recited in claim 1, wherein an accumulator, formed to provide voluminal adjustment by expansion and contraction within said hydraulic cylinder, is positioned between said first piston head and said opposing second piston head.

3. The adjustable hydraulic damper apparatus for use with a prosthetic knee joint, as recited in claim 2, wherein said accumulator is formed of an annular ring of compressible, closed cell foam, which is positioned about a portion of the piston member connecting said first and second piston heads.

4. An adjustable hydraulic damper apparatus, comprising:
   a. a hydraulic cylinder, having a longitudinal bore forming a cylinder wall having an inner surface and an outer surface, said cylinder wall being formed of a resilient material;
   b. hydraulic fluid located within said longitudinal bore of said hydraulic cylinder;
   c. a piston member, having at least one piston head which is longitudinally movable in said longitudinal bore;

d. wherein an annular space is defined by an outer cylindrical surface of said piston head and said inner surface of said cylinder wall, said annular space forming a peripheral valve through which said hydraulic fluid passes upon movement of said piston head within said hydraulic cylinder; and e. means for variably deforming said inner surface of said cylinder wall, thereby varying said annular space of said peripheral valve, which include:
  (1) an annular ramp formed circumferentially about, and extending outward of, said outer surface of said cylinder wall, said annular ramp having an angled bearing surface;
  (2) a threaded portion on said outside surface of said cylinder wall;
  (3) a nut member, internally threaded to rotatingly engage said threaded portion on said outside surface of said cylinder wall, said nut member having an angled inside circumferential surface formed to bear, when said nut member is rotated, upon said angled bearing surface of said annular ramp;
  (4) said cylinder wall being formed, when said angled surface of said nut member bears upon said bearing surface of said annular ramp, to create an annular deformation of said inside surface of said cylinder wall;
  (5) said annular deformation having a magnitude controlled by the rotation of said nut member.

5. The adjustable hydraulic damper apparatus, as recited in claim 4, wherein:
  a. said piston member includes:
    (1) two opposing piston heads, a first piston head and a second piston head;
    (2) each piston head additionally having an internal valve;
  b. said adjustable hydraulic damper apparatus being formed so that:
    (1) with movement of said piston member in a first direction, said internal valve of said first piston head is closed with hydraulic fluid flowing through said peripheral valve of said first piston head; and said internal valve of said second piston head is open with hydraulic fluid flowing through said internal valve of said second piston head; said peripheral valve of said first piston head controlling said movement of said piston member in said first direction; and
    (2) with movement of said piston member in a second direction, opposing said first direction, said internal valve of said second piston head is closed with hydraulic fluid flowing through said peripheral valve of said second piston head; and said internal valve of said first piston head is open with hydraulic fluid flowing through said internal valve of said first piston head; said peripheral valve of said second piston head controlling said movement of said piston member in said second direction.

6. The adjustable hydraulic damper apparatus, as recited in claim 5, wherein said internal valve is formed of a plurality of longitudinal interior passageways and a flexible baffle located adjacent to an end of said longitudinal interior passageways.

7. The adjustable hydraulic damper apparatus, as recited in claim 5, wherein an accumulator, formed to provide voluminal adjustment by expansion and contraction within said hydraulic cylinder, is positioned between said first piston head and said opposing second piston head.

8. The adjustable hydraulic damper apparatus, as recited in claim 7, wherein said accumulator is formed of compressible material which is positioned about a portion of the piston member connecting said first and second piston heads.

9. The adjustable hydraulic damper apparatus, as recited in claim 8, wherein said compressible material of said accumulator is formed of an annular ring of closed cell foam.

10. An adjustable hydraulic damper apparatus, comprising:
  a. a hydraulic cylinder, having a longitudinal bore forming a cylinder wall having an inner surface and an outer surface, said cylinder wall being formed of a resilient material;
  b. hydraulic fluid located within said longitudinal bore of said hydraulic cylinder;
  c. a piston member, having at least one piston head which is longitudinally movable in said longitudinal bore;
  d. wherein an annular space is defined by an outer cylindrical surface of said piston head and said inner surface of said cylinder wall, said annular space forming a peripheral valve through which said hydraulic fluid passes upon movement of said piston head within said hydraulic cylinder; and
  e. means for variably deforming said inner surface of said cylinder wall, thereby varying said annular space of said peripheral valve, which include:
    (1) an annular projection formed circumferentially about, and extending outward of, said outer surface of said cylinder wall, said annular projection having a bearing surface thereon;
    (2) a threaded portion on said outside surface of said cylinder wall;
    (3) a nut member, internally threaded to rotatingly engage said threaded portion on said outside surface of said cylinder wall, said nut member having a circumferential surface formed to bear, when said nut member is rotated, upon said bearing surface of said annular projection on the outside surface of said cylinder wall;
    (4) said cylinder wall being formed, when said circumferential surface of said nut member bears upon said bearing surface of said annular projection on the outside surface of said cylinder wall, to create an annular deformation of said inside surface of said cylinder wall;
    (5) said annular deformation having a magnitude controlled by the rotation of said nut member.

* * * * *